United States Patent [19]
Roth

[11] Patent Number: 5,578,757
[45] Date of Patent: Nov. 26, 1996

[54] METHOD OF POISSON'S RATIO IMAGING WITHIN A MATERIAL PART

[75] Inventor: Don J. Roth, Lakewood, Ohio

[73] Assignee: The United States of America as represented by the Administrator of the National Aeronautics and Space Administration, Washington, D.C.

[21] Appl. No.: 288,364

[22] Filed: Aug. 9, 1994

[51] Int. Cl.⁶ .................................................. G01N 29/00
[52] U.S. Cl. ........................................... 73/597; 73/599
[58] Field of Search .......................... 73/597, 599, 606, 73/607, 618

[56] References Cited

U.S. PATENT DOCUMENTS

| | | | |
|---|---|---|---|
| 3,302,044 | 1/1967 | Lynnworth et al. | |
| 3,822,587 | 7/1974 | Makino et al. | 73/597 |
| 4,213,147 | 7/1980 | Von Buenau | 358/112 |
| 4,362,058 | 12/1982 | Abele | 73/599 |
| 4,967,401 | 10/1990 | Barney | 367/46 |
| 5,038,787 | 8/1991 | Antich et al. | 128/660.01 |
| 5,099,848 | 3/1992 | Parker et al. | 73/575 |
| 5,181,421 | 1/1993 | Kline | 73/597 |

*Primary Examiner*—Richard Chilcot
*Assistant Examiner*—Max H. Noori
*Attorney, Agent, or Firm*—Vernon E. Williams; Kent N. Stone; Susan Reinecke

[57] ABSTRACT

The present invention is directed to a method of displaying the Poisson's ratio image of a material part. In the present invention longitudinal data is produced using a longitudinal wave transducer and shear wave data is produced using a shear wave transducer. The respective data is then used to calculate the Poisson's ratio for the entire material part. The Poisson's ratio approximations are then used to displayed the image.

6 Claims, 3 Drawing Sheets

METHOD OF POISSON'S RATIO IMAGING WITHIN A MATERIAL PART

ORIGIN OF THE INVENTION

The invention described herein was made by an employee of the United States Government and may be manufactured and used for the Government for governmental purposes without the payment of any royalties thereon or therefore.

FIELD OF THE INVENTION

The present invention is directed to a method and apparatus for determining Poisson's ratio variation within a material part so that it can be displayed for analysis. Poisson's ratio variations within a material part have been found to contribute to the structural failure of a material part. Poisson's ratio variations in the form of a pictorial map within the material part were previously unattainable without using intrusive methods. Therefore, in performing prior art numerical analysis the Poisson's ratio was assumed to be constant, thereby creating a less accurate numerical analysis of the material part.

It is, therefore, an object of the present invention to interrogate the material part using an improved contact scan method that permits dry inspection.

It is a further object of the invention to create accurate numerical analysis by providing the Poisson's variation within the material part.

It is still a further object of the invention to display the Poisson's variation within the material part by imaging.

DESCRIPTION OF RELATED ART

U.S. Pat. No. 3,302,044 relates to an ultrasonic probe which is able to detect both longitudinal waves and shear waves. U.S. Pat. No. 4,213,147 is directed to ultrasonic image processing of B scan ultrasonic images. U.S. Pat. No. 4,967,401 relates to an analysis of seismic data used to locate hydrocarbon reservoirs by determining lithographic parameters including Poisson's ratio. U.S. Pat. No. 5,038,787 is directed to an ultrasonic inspection system directed for the evaluation of bone structures which takes into account Poisson's ratio.

SUMMARY OF THE INVENTION

The present invention is directed to a method of determining the Poisson's ratio variation within a material part. A self-aligning transducer assembly is used to perform the ultrasonic contact scan. The assembly enables dry coupled contact scanning of the material part. The assembly is designed using buffer rod faces so that the transducer head will make contiguous contact with the material part. The transducer assembly is then moved repeatedly across the surface of the material part to attain a full image of the entire material part.

The measurements are used to determine the poisson's ratio variation within a material part. The Poisson's ratio variation is desired when doing finite element analysis of the material part for more accurate modeling. In the present disclosure, a Poisson's ratio image is generated by taking discrete measurements of both the ultrasonic longitudinal wave velocity and the shear wave velocity of the material part. The Poisson's ratio is computed as $v=[(vl^2/2-vs^2)/(vl^2-vs^2)]$ for each point selected. The poisson value for each point is mapped to a gray scale and imaged using the scale values.

BRIEF DESCRIPTION OF THE DRAWINGS

The objects, advantages, and novel features of the invention will be more fully apparent from the following detailed description when read in connection with the accompanying drawings in which.

DESCRIPTION OF THE PREFERRED EMBODIMENT

Figure 1:
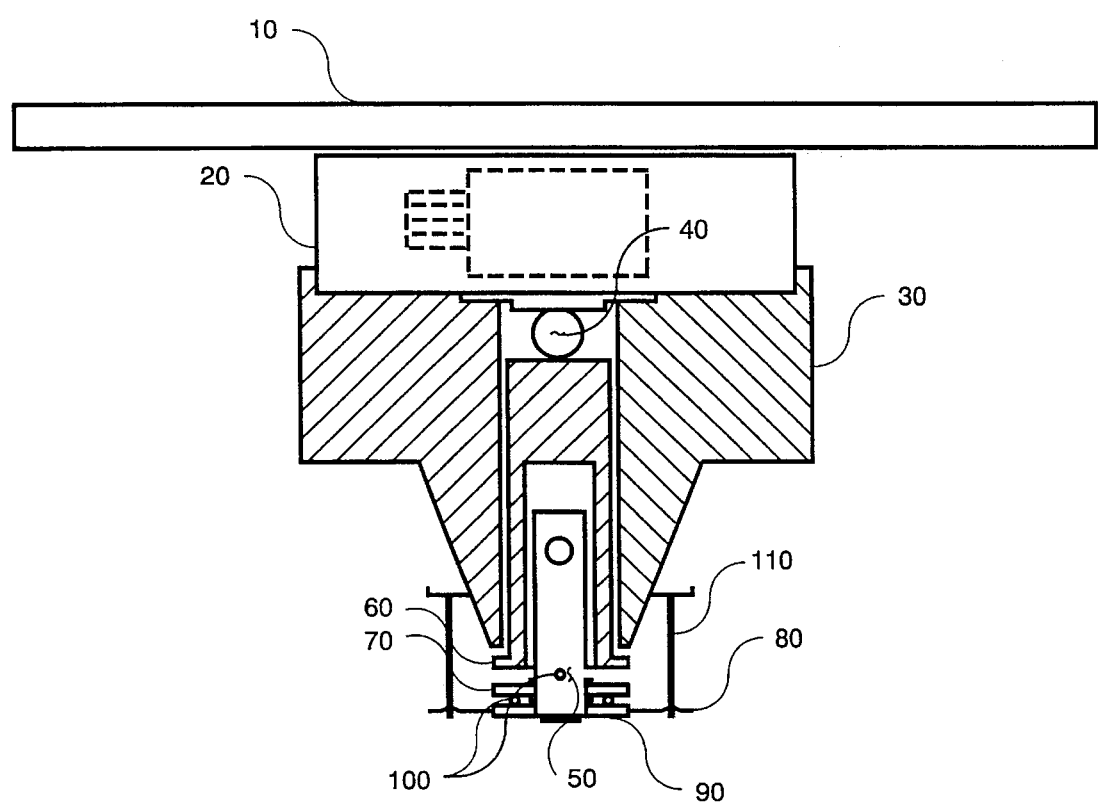
FIG. 1. displays a drawing of the self-aligning transducer assembly for ultrasonic contact scanning.

FIG. 1. displays the transducer sensor assembly. A mounting plate 10 supports the assembly so that the entire assembly can be positioned. A load cell 20 attaches the mounting plate to the housing of the assembly 30. The housing 30 retains a sleeve 60 which in turn retains the transducer 50. A ball bearing 40 is used to maintain slidable contact between the load cell 20 and the sleeve 60. A middle ring 70 and a bottom ring 90 are separated by bearing balls 100. The complete assembly is held together by retainer bands 110 attached to retainer pins 80.

Figure 2:
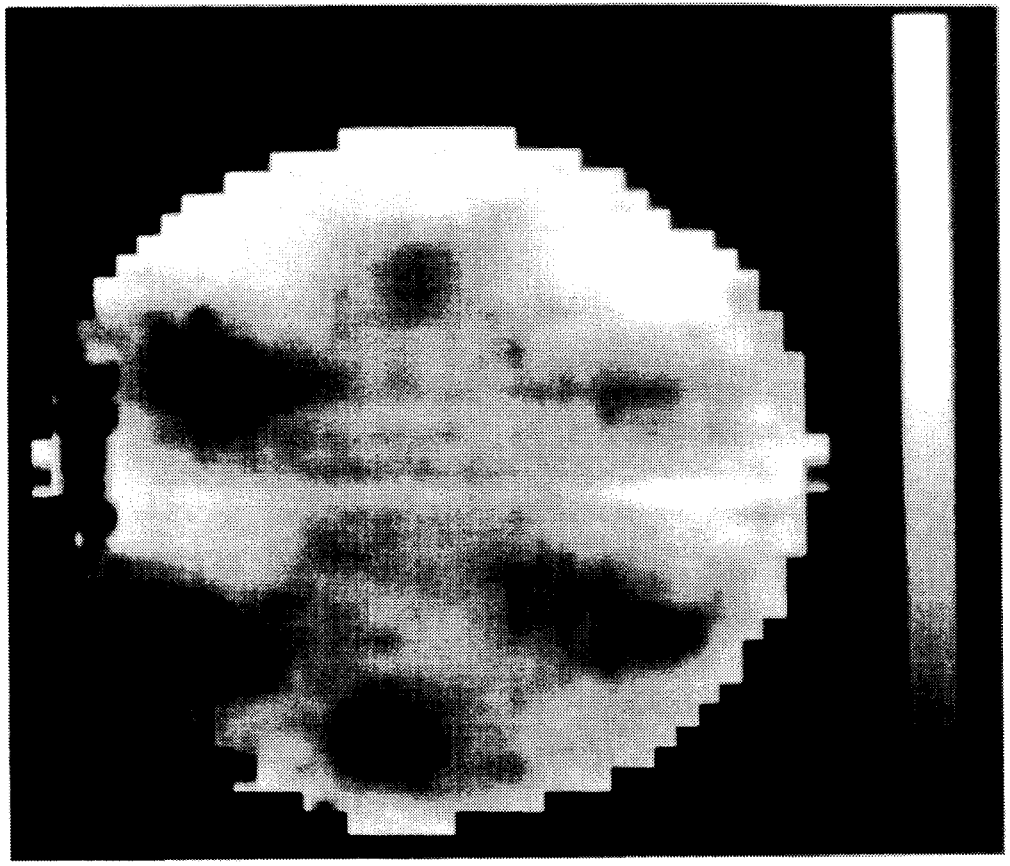
FIG. 2. displays a photo-micrograph of the poisson ratio variation within a material part.

FIG. 2. displays an image of the Poisson's ratio within a material part. To obtain the image the ultrasonic probe systematically scans each area of the material part.

Figure 3:
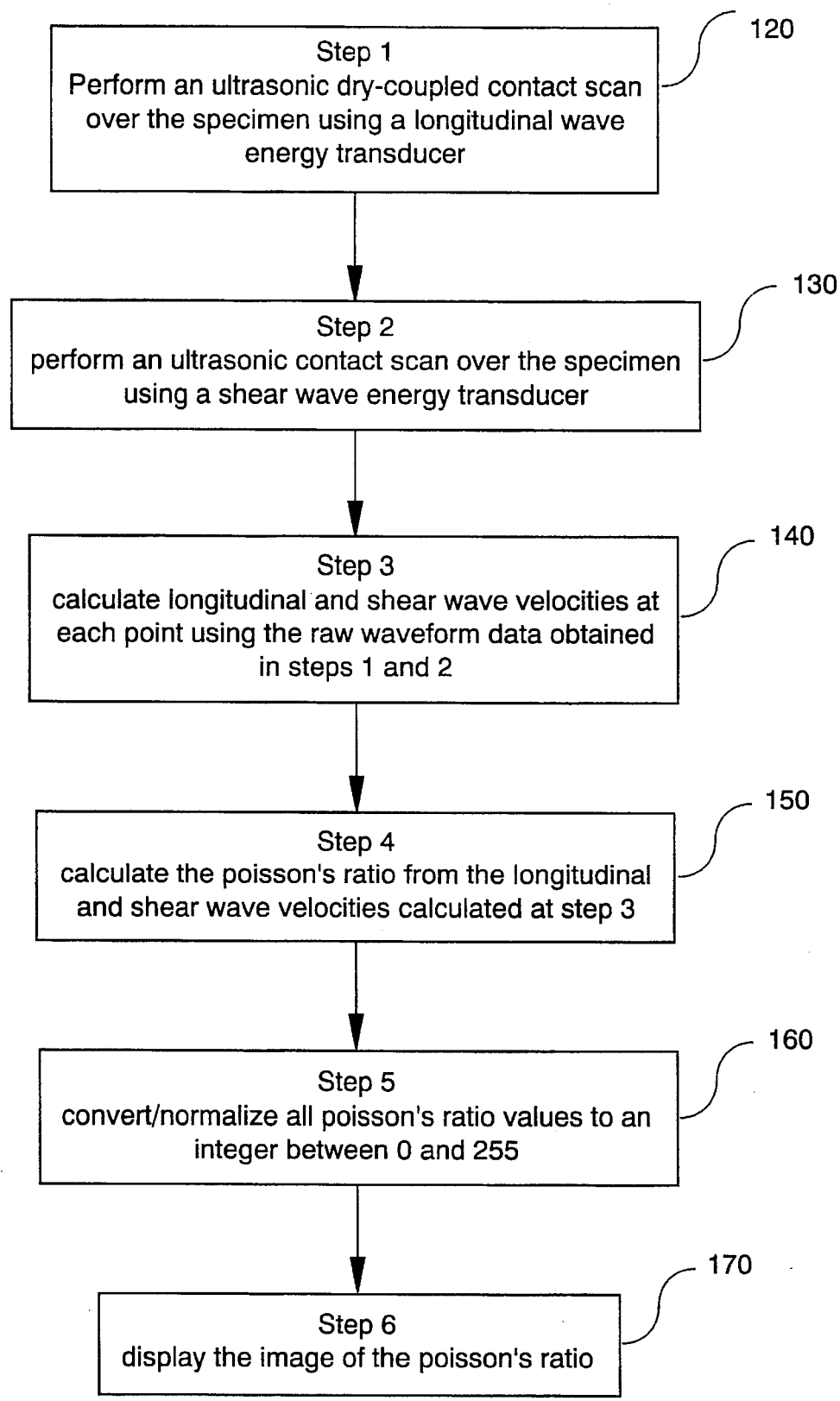
FIG. 3. displays a flow chart of the method used to measure the poisson ratio variation within a material part.

The image is created by performing several steps detailed in the flow chart of FIG. 3. First an ultrasonic contact scan is made over the portion of a sample that is of interest. The first scan is performed by using a longitudinal wave energy transducer as denoted by 120. The scan method performed can either be a wet or a dry coupled scan, however the dry coupled scan would be more consistent with the spirit of the invention. Next a second scan of the sample portion of interest is scanned using a shear wave energy transducer as denoted by 130. The best results are attained if the nominal transducer frequency used in the longitudinal wave is used in the shear wave. The data from the measurement are used to calculate the longitudinal and shear wave velocities at each scan point as denoted by 140. The Poisson's ratio is then calculated using the formula $v=[(vl^2/2-vs^2)/(vl^2-vs^2)]$. The Poisson's ratio value for each measured point is then converted to normalize the value to an integer value between 0 and 255 as denoted by 160. The largest and smallest values of the Poisson's ratio should be set to 255 and 0, respectively to begin the normalization process. As a final step the poisson's image is displayed using an 8-bit (256 value) video image processing system as denoted by 170.

While the preferred embodiment of the invention is disclosed and described it will be apparent that various modifications may be made without departing from the spirit of the invention or the scope of the subjoined claims.

What is claimed:

1. A method of imaging Poisson's ratio variation within a material part, comprising the steps of:

performing a first scan over a material part using a longitudinal wave energy transducer thereby producing longitudinal data, performing a second scan over said material part using a shear wave energy transducer, thereby producing shear wave data, approximating longitudinal velocities using said longitudinal data, approximating said shear wave velocities using said shear wave data, approximating Poisson's ratios using the relationship: $v=[(vl^2/2-vs^2)/(vl^2-vs^2)]$, where (vl) is said longitudinal velocity and (vs) is said shear wave velocity, normalizing said Poisson's ratios thereby producing normalized data, and displaying said normalized data therby imaging said Poisson's ratio variation within said material part.

2. A method as claimed in claim 1 wherein normalized data is normalized to integer values between 0 and 255.

3. A method as claimed in claim 1 wherein said normalized data is displayed using an 8-bit video image processing system.

4. A method as claimed in claim 1 wherein said normalized data is mapped to a grey scale.

5. A method as claimed in claim 1 wherein said first scan is performed using dry-coupling.

6. A method as claimed in claim 1 wherein said second scan is performed using dry-coupling.

* * * * *